United States Patent [19]
Vidal et al.

[11] Patent Number: 5,441,509
[45] Date of Patent: Aug. 15, 1995

[54] VESSEL CLIPS

[75] Inventors: Claude Vidal, Santa Barbara; Russell J. Redmond, Goleta; John M. Barker, Ventura; Mike Collinson, Goleta, all of Calif.; Eric J. Donaldson, St. Paul, Minn.; Alan J. Solynties, Richfield, Minn.; Robert M. Eyerly, Lino Lakes, Minn.

[73] Assignee: Minnesota Mining and Manufacturing Company, St. Paul, Minn.

[21] Appl. No.: 336,565

[22] Filed: Nov. 9, 1994

Related U.S. Application Data

[63] Continuation of Ser. No. 875,060, Apr. 28, 1992, abandoned.

[51] Int. Cl.⁶ ............................................. A61B 17/08
[52] U.S. Cl. .................................... 606/151; 606/157; 606/158; 24/326; 24/115 A; 24/703.1
[58] Field of Search ............... 606/143, 151, 157, 158; 24/115 A, 326, 445, 446, 703.1

[56] References Cited

U.S. PATENT DOCUMENTS

| | | |
|---|---|---|
| 1,625,602 | 3/1927 | Gould et al. . |
| 2,256,382 | 9/1941 | Dole . |
| 2,277,139 | 3/1942 | Neimand . |
| 2,758,302 | 8/1956 | White . |
| 3,326,216 | 6/1967 | Wood . |
| 3,378,010 | 4/1968 | Codling et al. . |
| 3,604,067 | 9/1971 | Brown ............................... 24/326 |
| 3,687,131 | 8/1972 | Rayport et al. ..................... 606/157 |
| 3,699,957 | 10/1972 | Robinson . |
| 3,708,149 | 2/1973 | Dinger . |
| 3,713,533 | 1/1973 | Reimels . |
| 3,777,538 | 12/1973 | Weatherly et al. . |
| 3,856,016 | 12/1974 | Davis . |
| 3,867,944 | 2/1975 | Samuels . |
| 3,882,854 | 5/1975 | Hulka et al. . |
| 3,899,914 | 8/1975 | Akiyama . |
| 3,954,108 | 5/1976 | Davis . |
| 3,996,937 | 12/1976 | Williams . |
| 4,024,868 | 5/1977 | Williams . |
| 4,152,920 | 5/1979 | Green . |
| 4,217,902 | 8/1980 | March . |
| 4,229,244 | 11/1981 | Noiles . |
| 4,242,902 | 1/1981 | Green . |
| 4,372,316 | 2/1983 | Blake, III et al. . |
| 4,399,810 | 8/1983 | Samuels et al. . |
| 4,414,721 | 11/1983 | Hufnagel . |
| 4,434,795 | 3/1984 | Mericle . |
| 4,444,187 | 4/1984 | Perlin . |
| 4,449,530 | 5/1984 | Bendel et al. . |
| 4,458,682 | 7/1984 | Cerwin . |
| 4,476,865 | 10/1984 | Failla et al. . |
| 4,522,207 | 6/1985 | Klieman et al. . |
| 4,556,060 | 12/1985 | Perlin . |
| 4,586,503 | 5/1986 | Kirsch et al. .................. 606/151 |
| 4,616,651 | 10/1986 | Golden ........................... 606/142 |
| 4,620,541 | 11/1986 | Gertzman et al. . |
| 4,658,822 | 4/1987 | Kees, Jr. . |
| 4,660,558 | 4/1987 | Kees, Jr. . |
| 4,671,281 | 6/1987 | Beroff et al. . |
| 4,702,247 | 10/1987 | Blake, III et al. ................ 606/157 |
| 4,765,335 | 8/1988 | Schmidt et al. . |
| 4,777,950 | 10/1988 | Kees, Jr. . |
| 4,799,481 | 1/1989 | Transue et al. . |
| 4,805,618 | 2/1989 | Ueda et al. ..................... 128/346 |
| 4,844,066 | 7/1989 | Stein . |
| 4,938,765 | 7/1990 | Rasmusson . |

(List continued on next page.)

FOREIGN PATENT DOCUMENTS

| | | |
|---|---|---|
| 0406014A1 | 1/1991 | European Pat. Off. . |
| 882601 | 7/1953 | Germany . |
| 1186283 | 1/1965 | Germany .................. 24/115 A |
| 2180455 | 10/1965 | United Kingdom . |
| 1389762 | 4/1988 | U.S.S.R. . |

*Primary Examiner*—Gary Jackson
*Attorney, Agent, or Firm*—Gary L. Griswold; Walter N. Kirn; Jeffrey J. Hohenshell

[57] ABSTRACT

A surgical clip for occluding an anatomical structure is disclosed. The clip has a hinge portions and at least three legs projecting from the hinge portion with a slot portion present between at least two of the legs. The hinge portion affords easy removal of the clip.

16 Claims, 5 Drawing Sheets

U.S. PATENT DOCUMENTS

| | | |
|---|---|---|
| 4,976,722 | 12/1990 | Failla . |
| 4,979,950 | 12/1990 | Transue et al. ............... 606/158 |
| 5,026,379 | 6/1991 | Yoon . |
| 5,026,382 | 6/1991 | Peiffer . |
| 5,053,045 | 10/1991 | Schmidt et al. . |
| 5,062,846 | 11/1991 | Oh et al. . |
| 5,066,288 | 11/1991 | Deniega et al. ............... 604/274 |
| 5,084,057 | 1/1992 | Green et al. ............... 606/142 |
| 5,092,870 | 3/1992 | Mittermeier ............... 606/151 |
| 5,100,420 | 3/1992 | Green et al. ............... 606/143 |
| 5,104,394 | 4/1992 | Knoepfler . |
| 5,104,395 | 4/1992 | Thornton et al. . |

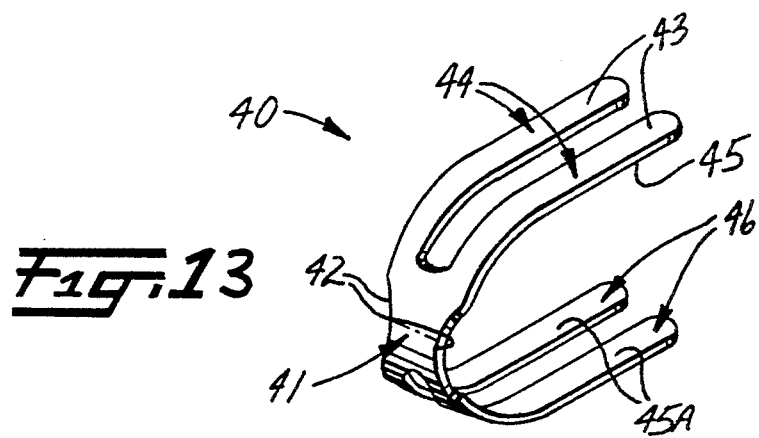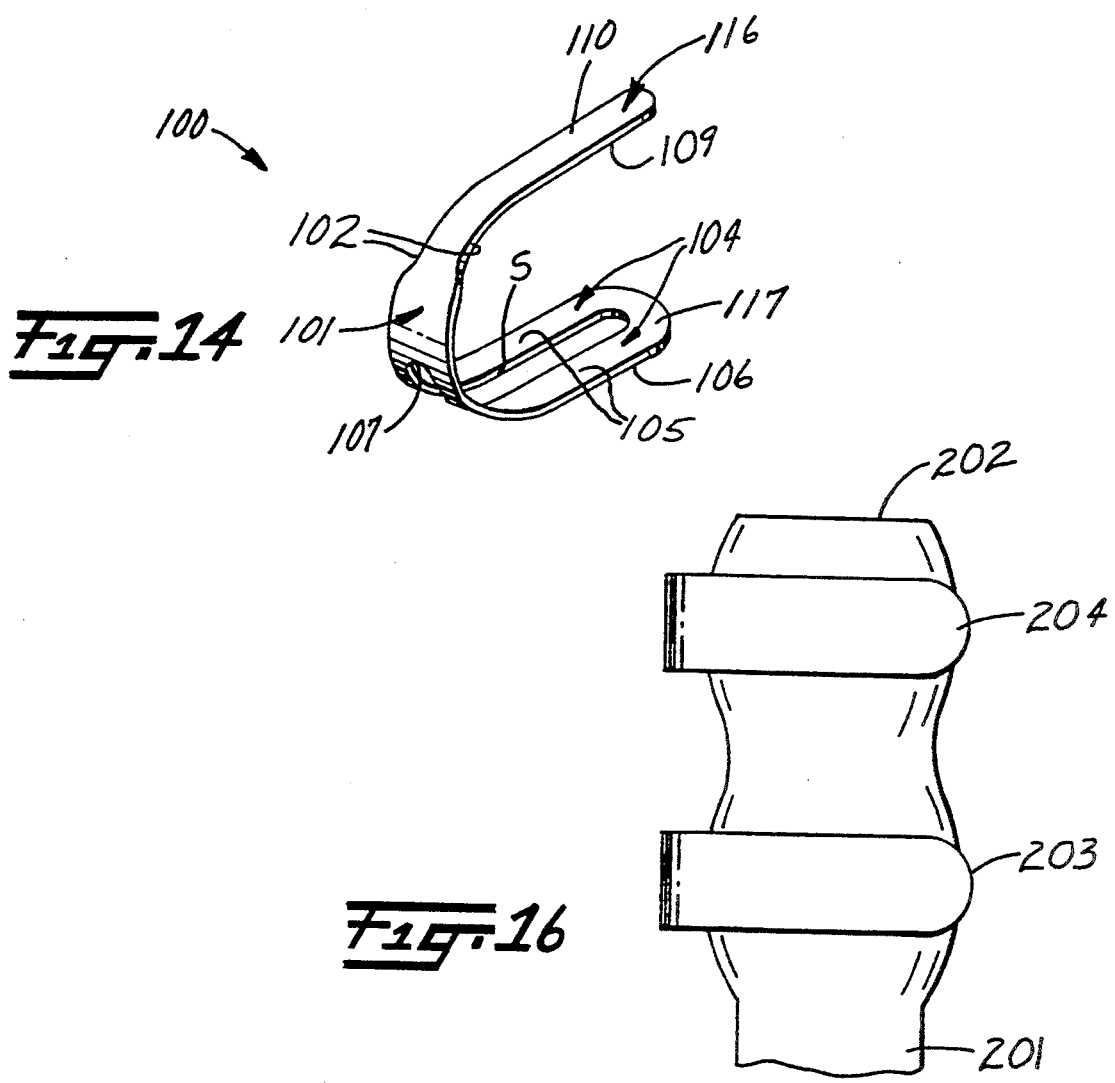

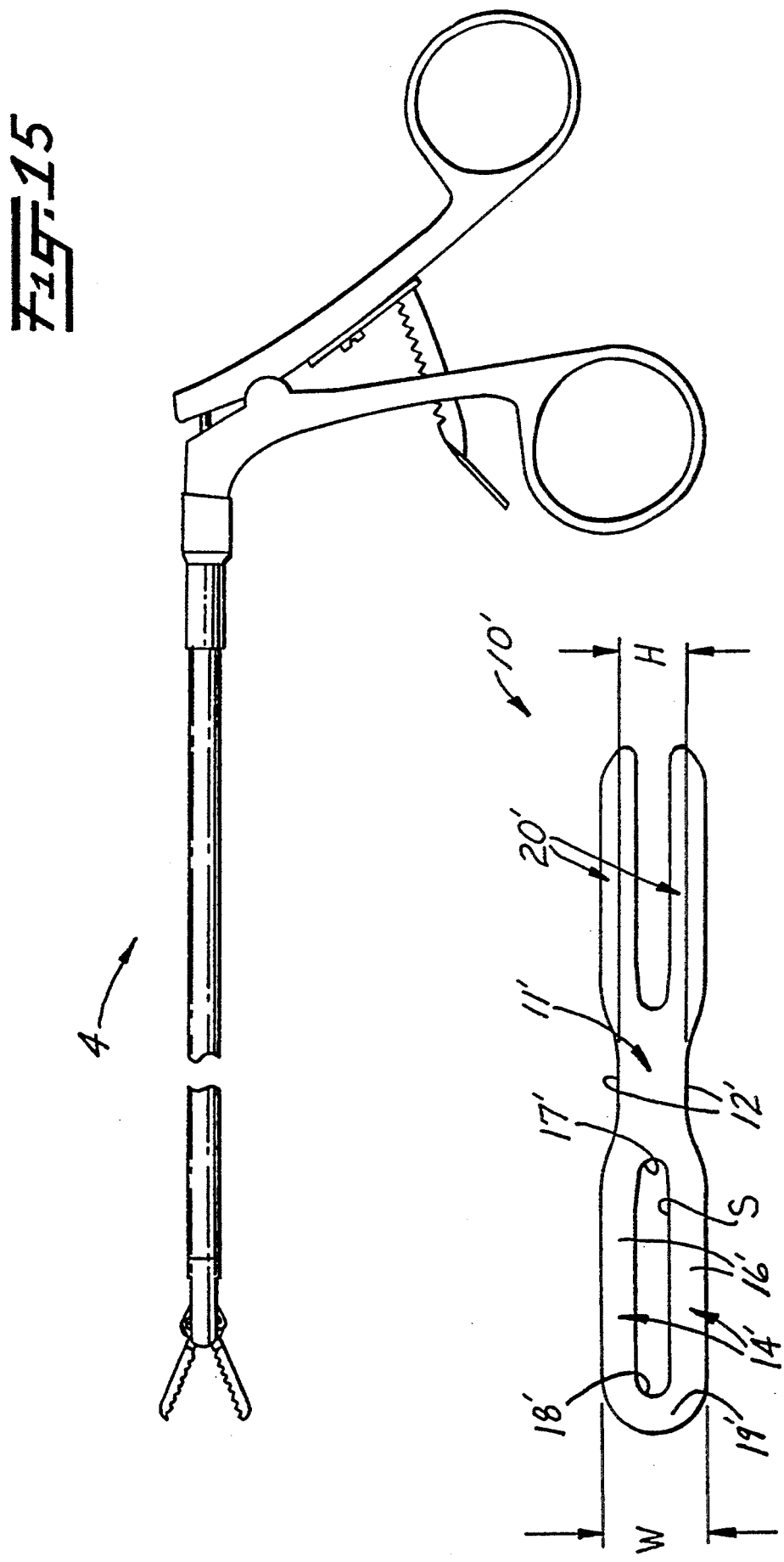

VESSEL CLIPS

This is a continuation application of application Ser. No. 07/875,060 filed Apr. 28, 1992, now abandoned.

TECHNICAL FIELD

The present invention relates generally to devices for occluding tubular structures and more particularly to surgical clips for occluding tubular body structures.

BACKGROUND OF THE INVENTION

The art is replete with clips for use in surgical procedures. Examples of surgical clips are shown in U.S. Pat. Nos. 4,434,795, 4,476,865, 4,616,651, 4,620,541, 4,671,281, 4,556,060, 5,062,846, and 5,026,379.

Some surgical clips have a biasing means for biasing the clip toward a clamped configuration. Examples of such clips are found in U.S. Pat. No.'s 3,996,937, 4,024,868, 4,444,187, 4,658,822, 4,660,558, 4,777,950, and 5,053,045. However, such clips are generally not used in every application.

A typical malleable surgical clip is shown, for example, in U.S. Pat. No. 3,713,533. That clip is initially provided in an unclamped position. The clip includes a pair of legs that are plastically deformable by a clip applier tool from the initial, unclamped position to a clamped position.

Other malleable, plastically deformable surgical clips are shown, for example, in U.S. Pat. Nos. 4,449,530, 4,702,247, 4,799,481, 4,844,066, 4,976,722, 4,979,950 and 5,026,382. Examples of clip applier tools are shown in U.S. Pat. Nos. 3,856,016, 3,954,108, 4,242,902, 4,299,224, 5,084,057 and 5,100,420 the entire contents of which are herein expressly incorporated by reference.

Surgical clips such as those shown in U.S. Pat. No. 3,713,533 tend to have difficulty in occluding tubular anatomical structures during some applications. In those applications, such clips tend to slip or slide off the tubular structure either intra-operatively or post-operatively with undesirable results for the patient.

The tendency for prior art clips to slide or slip off a tubular structure is particularly a problem when the single legged clips are used in a procedure where the tubular structure is both clipped and cut. FIG. 16 illustrates an anatomical tubular structure 201 (such as a vessel) which is "divided" or cut at end 202. Typically, a surgeon may use two, individual prior art clips 203 and 204 to clip the structure 201. Because clip 204 is in close proximity to cut end 202, there is a chance that the clip 204 may separate from the tubular structure 201 resulting in undesirable consequences for the patient.

While in some instances surgical clips may be left permanently within the patients' body, in some surgical procedures, the surgical clips are removed from the tubular structure (e.g. a vessel) before the surgical procedure is completed. A general purpose tool generally known as the "Grasper" generally available from Karl Storz, Germany is used to remove a surgical clip. An example of such a clip removal tool is shown in FIG. 15.

U.S. Pat. Nos. 3,856,016 and 3,954,108 disclose a single surgical clip which is said to constitute in effect two occlusion clips for use in, for example, occluding fallopian tubes. When such clips are used to occlude fallopian tubes they are generally intended to remain on the fallopian tubes permanently. Moreover, it is believed that such clips would be difficult to safely remove from the tubular structure. To remove such a clip from the tubular structure, typically the surgeon would either (1) grasp only one leg which results in an asymmetric removal force which may damage tissue, or (2) grasp both legs simultaneously which may be difficult to accomplish due to the lack of structure at the hinge portion between the legs and due to the potential for the hinge to collapse (also as a result of the lack of structure at the hinge portion).

DISCLOSURE OF THE INVENTION

The present invention provides a surgical clip which affords (1) secure, effective and efficient occlusion of tubular anatomical structures by affording extrusion of the tubular structure between and even above a pair of clip legs, (2) convenient and efficient removal of the surgical clip from the tubular anatomical structure, (3) a durable and strong hinge portion capable of resisting bending, collapse, skewing or twisting, (4) surfaces adapted to be engaged by a clip removal tool for convenient removal of the clip from the tubular structure, (5) clip placement and retention at a location closely adjacent the cut end of a tubular structure and (6) time savings during a surgical procedure, including the time it takes to place and remove a clip during a surgical procedure.

According to the present invention, there is provided a surgical clip for occluding tubular structures that are elongate in a first direction. The clip comprises a unitary, monolithic hinge portion having removal surfaces adapted to be engaged by a tool for removing the clip from the tubular structure. The clip includes a first leg portion having a pair of first legs projecting from the hinge portion. The first legs have vessel engaging surfaces, and clip applier bearing surfaces opposite the vessel engaging surfaces.

The first legs are spaced apart a first distance to provide a vessel tissue extrusion slot extending between and opening through the vessel engaging and clip applier bearing surfaces. The slot has first and second ends. At least the first end is a closed end formed by the hinge portion.

The clip also includes a second leg portion having at least one second leg projecting from the hinge portion and away from the first leg portion. The at least one second leg has vessel engaging surfaces, and clip applier bearing surfaces opposite the vessel engaging surfaces.

The clip is generally plastically deformable between (1) an unclamped position with the vessel engaging surfaces of the second leg portion spaced from the vessel engaging surfaces of the first leg portion and (2) a clamped position with (a) the vessel engaging surfaces of the first and second leg portions spaced closer together than in the unclamped position, (b) the tubular structure compressed between the vessel engaging surfaces of the first and second leg portions, and (c) tissue situated within the slot.

The hinge portion has structure located between the first legs to define the closed first end of the slot. The removal surfaces are situated so that the clip removal tool may provide a removal force generally perpendicular to the "first direction" (the direction of elongation of the vessel) to afford easy removal of the clip when the clip is in the clamped position.

BRIEF DESCRIPTION OF THE DRAWING

The present invention will be further described with reference to the accompanying drawing wherein like reference numerals refer to like parts in the several views, and wherein:

FIG. 13 is a perspective view of a clip formed by bending the blank of FIG. 5 into a shape that affords insertion into the open jaws of a clip applier;

FIG. 14 is a perspective view of a clip formed by bending the blank of FIG. 11 into a shape that affords insertion into the open jaws of a clip applier;

FIG. 15 is a side view of a clip removal tool adapted to remove a clip according to the present invention from an anatomical tubular structure;

FIG. 16 is a fragmentary view of a pair of prior art clips placed on a tubular structure that has been cut at one end; and FIG. 17 is a plan view of a blank that may be used to form a tenth embodiment of surgical clip according to the present invention, illustrating vessel engaging surfaces.

DETAILED DESCRIPTION

Figure 2:
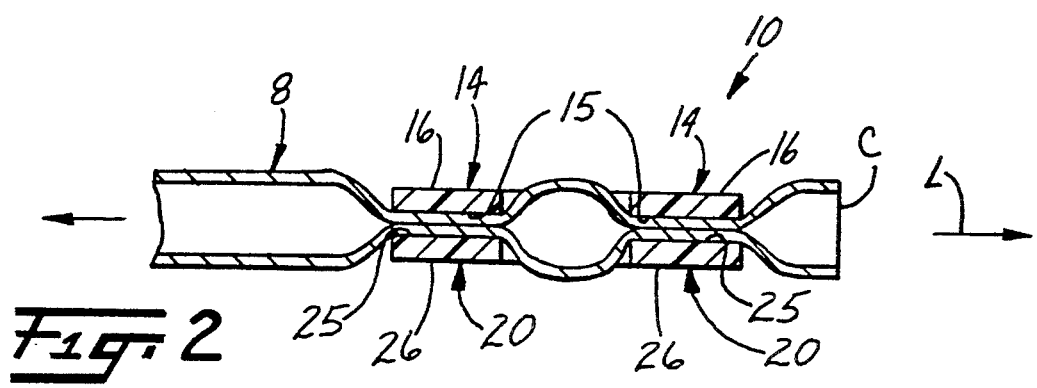
FIG. 2 is a section view of the surgical clip and tubular structure of FIG. 1 taken approximately along lines 2—2 of FIG. 1.

Referring now to FIGS. 1, 2, 4 and 12 of the drawing, there is shown a first embodiment of surgical clip according to the present invention and generally designated by the reference character 10.

The surgical clip 10 affords occlusion of a tubular anatomical structure 8, such as a vessel, that is elongate in a first direction L (FIG. 2). The clip 10 may be used, for example, in a surgical procedure where the structure is cut at end C.

The surgical clip 10 preferably comprises a unitary, monolithic hinge portion 11 having removal surfaces 12 adapted to be engaged by a tool 4 (see e.g. FIG. 15) for removing the clip 10 from the tubular structure 8.

The tool 4 for removing the clip from the tubular structure 8 is shown in FIG. 15. The tool 4 may comprise, for example, a multipurpose "Grasper" generally available from Karl Storz, Germany.

The clip 10 has a first leg portion having a pair of first legs 14 projecting from the hinge portion 11. The first legs 14 have proximal and distal ends relative to the hinge portion 11, vessel engaging surfaces 15, and clip applier bearing surfaces 16 opposite the vessel engaging surfaces 15.

The first legs 14 are spaced apart a first distance D to provide a vessel tissue extrusion slot S extending between and opening through the vessel engaging 15 and clip applier bearing 16 surfaces. The slot S has first 17 and second 18 ends. The first end 17 is a closed end formed by the hinge portion 11. The hinge portion 11 provides a strong, secure, durable structure that may be conveniently engaged or "grasped" by a clip removal tool 4 to remove the clip from the tubular structure 8 without unduly bending or twisting.

The first legs 14 are generally parallel to each other. The distal ends of the first legs 14 are connected by an arcuate distal end portion 19 and are integral therewith. The arcuate distal end portion 19 forms a second, closed end 18 of the slot S.

The clip 10 according to the present invention also has a second leg portion having at least one second leg 20 (and in the case of the clip 10, two legs 20) projecting from the hinge portion 11 and away from the first leg portion. The second legs 20 have proximal and distal ends, vessel engaging surfaces 25, and clip applier bearing surfaces 26 opposite the vessel engaging surfaces 25. The second legs 20 are generally parallel to each other and also include a slot S therebetween. The second legs 20 are connected at their distal ends by an arcuate distal end portion and are integral therewith.

Figure 1:
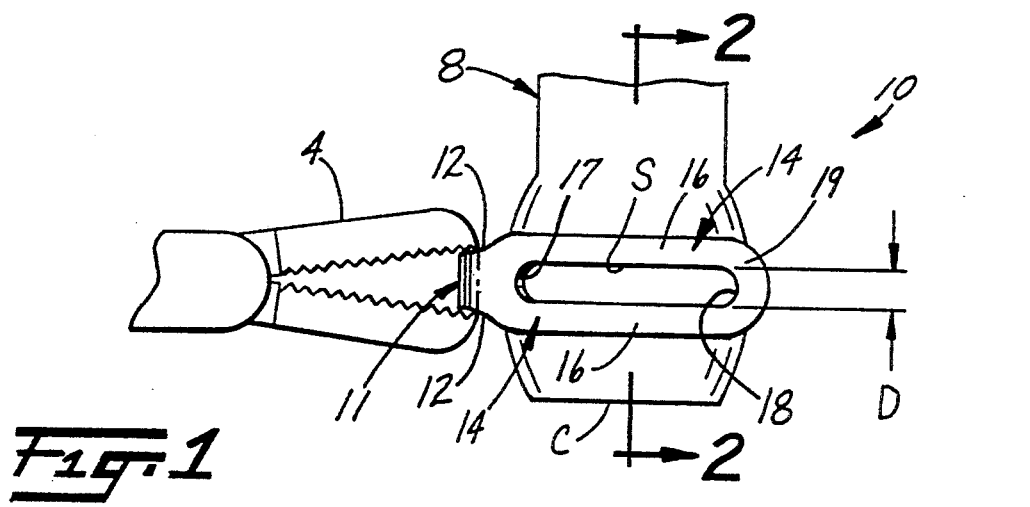
FIG. 1 is a fragmentary view of a first embodiment of surgical clip according to the present invention clamped on an anatomical tubular structure, and showing a tool for removing the clip from the tubular structure with portions broken away to show detail.

FIGS. 1 and 2 illustrate the clip 10 clamped near the cut end C of a tubular structure 8. The clip 10 may be situated and retained in close proximity to the cut end C of the vessel 8 since the legs 14 and 20 that are remote from the cut end C tend to retain the position of the legs 14 and 20 (relative to the vessel 8) that are adjacent the cut end C.

Preferably, the clip applier bearing surfaces 16 and 26 and the vessel engaging surfaces 15 and 25 of the first and second leg portions are generally flat, planar portions. Optionally, but not preferably, the vessel engaging surfaces 15 and 25 may comprise a structured surface such as the structured surface shown in U.S. Pat. No. 3,326,216 the entire contents of which are herein expressly incorporated by reference. Such structured surfaces on the vessel engaging surfaces may afford increased resistance to sliding off the vessel.

Also optionally, but not preferably, the clip applier bearing surfaces 16 and 26 may comprise a structured surface. Such structured surfaces of the clip applier bearing surfaces may afford more convenient handling by the clip applier tool.

The clip 10 is adapted to be placed between the closing jaws in a clip applier tool (not shown). The clips 10 may be used laparoscopically in a clip applier tool that is adapted to slide through the cannula of a trocar. Examples of such clip appliers are shown in U.S. Pat. No. 5,084,057 and U.S. Pat. No. 5,100,420.

Alternatively, the clips may be used in other types of clip appliers, such as those used in open surgery. Other examples of clip applier tools include U.S. Pat. No.'s 3,326,216, 3,713,533, 3,777,538, 3,856,016, 4,152,920, and 4,229,244 the entire contents of which are herein expressly incorporated by reference.

Figure 4:
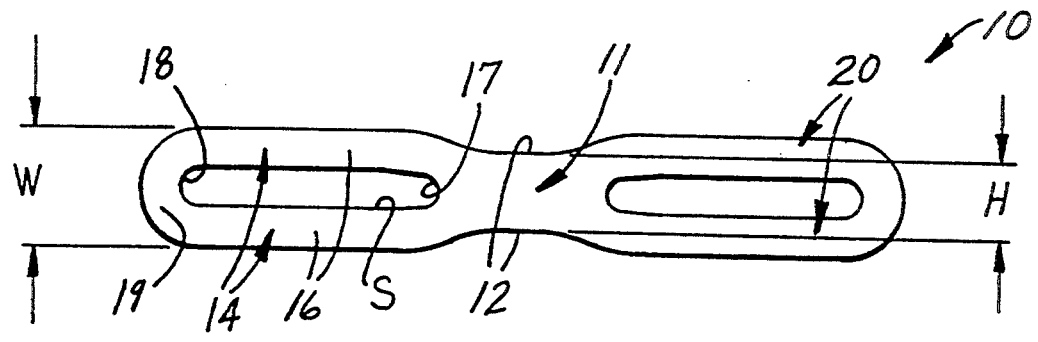
FIG. 4 is a plan view of a blank that may be used to form the first embodiment of surgical clip shown in FIGS. 1 and 2, illustrating clip applier bearing surfaces.
Figure 12:
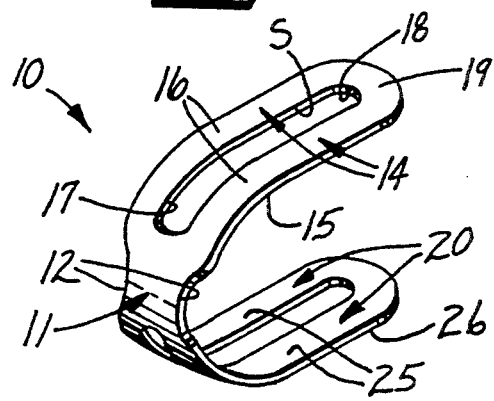
FIG. 12 is a perspective view of a clip formed by bending the blank of FIG. 4 into a shape that affords insertion into the open jaws of a clip applier.

Before the clip 10 is placed in the clip applier tool, the clip is bent from the blank shown in FIG. 4 to generally the shape shown in FIG. 12. The clip applier bearing surfaces 16 are adapted to engage the closing jaws of the clip applier tool. The clip 10 is generally plastically deformable by the clip applier tool between (1) an unformed or unclamped position (FIG. 12) with the vessel engaging surfaces 25 of the second leg portion spaced from the vessel engaging surfaces 15 of the first leg portion and (2) a clamped position (FIGS. 1 and 2).

In the clamped position, (1) the vessel engaging surfaces 15 and 16 of the first and second leg portions are spaced closer together than in the unclamped position, (2) the vessel or tubular structure S is compressed between the vessel engaging surfaces 15 and 25, and (3) tissue from the tubular structure 8 is situated or extruded into the slot S, and may even extrude above the clip applier bearing surfaces 16 as shown in FIG. 2.

The hinge portion 11 has structure located between the first legs 14 to define the closed first end 17 of the slot S. The removal surfaces 12 are situated so that the clip removal tool 4 may (1) provide a removal force generally perpendicular to the direction of elongation L of the vessel 8 to afford easy removal of the clip 10 when the clip 10 is in the clamped position, and (2) grasp the clip 10 at a location that is resistant to collapse. Alternatively, the clip removal tool 4 may grasp any portion of the hinge portion 11 or the clip 10 which the user finds convenient for removing the clip 10.

The first legs 14 have surfaces defining an outer leg width W, and the hinge portion has outer surfaces defining a hinge portion width H (FIG. 4). The outer leg width W is generally greater than the hinge portion width H, so that the clip 14 may be easily, conveniently and efficiently formed from the blank to both the unclamped and the clamped position.

The surgical clip 10 may be constructed in a variety of manners. For example, the clip 10 may be stamped from a sheet of fully annealed Titanium, ASTM F67-88, Grade 1, and then fashioned to the "unclamped" position using conventional stamping, coining (to soften or dull edges) and forming techniques well known to those skilled in the art. Alternatively, the clips may be constructed from Titanium CP (Commercially Pure) Grade 1 material.

For example, the clip may be constructed by (1) first creating the flat blank shown in FIG. 4, (2) then deburring the blank edges through coining, (3) forming the clip to the "unclamped" or U-shape shown in FIG. 12, and (4) then tumbling the clip for polish.

As an example not intended to be limiting, the clip 10 may have an overall length of approximately 0.696 inches (1.768 centimeters), a length of the hinge portion 11 of about 0.048 inches (0.122 centimeters), an overall thickness of about 0.012–0.016 inches, a width of about 0.105 inches (0.267 centimeters), and a width of the legs 14 and 20 of about 0.025 inches (0.064 centimeters). A version of this example with wider or "thicker" legs 14 and 20 would have a leg width of 0.035 inches and, correspondingly, a narrower or "thinner" slot S. Yet another version of this example may have a longer or thinner hinge portion 11.

Figure 3:
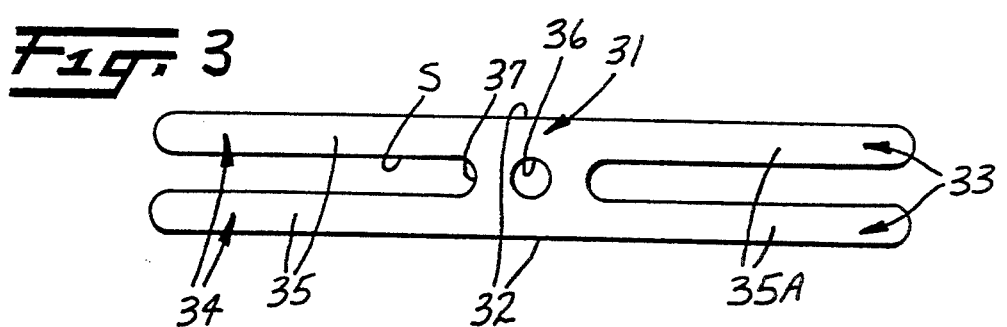
FIG. 3 is a plan view of a blank that may be used to form a second embodiment of surgical clip according to the present invention, illustrating vessel engaging surfaces.

Referring now to FIG. 3 of the drawing, there is shown a second alternative embodiment of a surgical clip according to the present invention, generally designated by the reference numeral 30 which has many parts that are essentially the same as the parts of the clip 10.

Like the clip 10, the clip 30 comprises a unitary, monolithic hinge portion 31 having removal surfaces 32 adapted to be engaged by the tool 4 for removing the clip 30 from the tubular structure. The clip 30 has a first leg portion having a pair of first legs 34 projecting from the hinge portion 31.

The first legs 34 have proximal and distal ends, vessel engaging surfaces 35, and clip applier bearing surfaces opposite the vessel engaging surfaces 35. The first legs 34 are spaced apart a first distance to provide a vessel tissue extrusion slot S extending between and opening through the vessel engaging 35 and clip applier bearing surfaces. The slot S has first 37 and second ends. The first end 37 is a closed end formed by the hinge portion 31.

Unlike the clip 10, in the clip 30, the second end of the slot S is an open end. In the clip 30, there is no distal end portion similar to the distal end portion 19 of clip 10. The absence of a distal end portion in the clip 30 is believed to provide a clip that is more readily removable from a tubular structure than the clip 10.

The clip 30 also has a second leg portion having two second legs 33 projecting from the hinge portion 31 and away from the first leg portion. The second legs 33 are generally identical to the first legs 34 so that the clip 30 is symmetrical about an imaginary line through the center of the hinge portion 31. The second legs 33 have proximal and distal ends, vessel engaging surfaces 35A, and clip applier bearing surfaces opposite the vessel engaging surfaces 35A. Like the clip 10 the clip 30 is generally plastically deformable between an unclamped position and a clamped position.

Unlike the hinge portion 11 of the clip 10, the hinge portion 31 of the clip 30 comprises a circular hole extending therethrough. The hole 36 provides a clip having an hinge portion which is easier to fashion from the blank to both the unclamped and to the clamped position but which nevertheless provides a strong, secure, durable structure that may be conveniently engaged or "grabbed" by a clip removal tool 4 to remove the clip from the tubular structure 8 without unduly bending or twisting.

Like the clip 10, in the clip 30, the hinge portion 31 has structure located between the first legs 34 to define the closed first end 37 of the slot S. The removal surfaces 32 are situated so that the clip removal tool 4 may provide a symmetrical removal force generally perpendicular to the direction of elongation of the vessel to afford easy removal of the clip 30 when the clip 30 is in the clamped position. Alternatively, the clip removal tool 4 may grasp any portion of the hinge portion 31 which the user finds convenient for removing the clip 30. Optionally, the hole 36 may be used as a "window"

to view surfaces on a side of clip 30 through the hinge portion 31.

Such a clip may be particularly desirable when used laparoscopically so that an endoscope with optical means may view the scene through the hole 36.

Also unlike the clip 10, in the clip 30, the first legs 14 have surfaces defining an outer leg width W, and the hinge portion has outer surfaces defining a hinge portion width H (FIG. 4). The outer leg width W is generally equal to the hinge portion width H.

As an example not intended to be limiting, the clip 30 may have an overall length of approximately 0.696 inches (1.768 centimeters), a length of the hinge portion 31 of about 0.056 inches (0.142 centimeters), an overall thickness of about 0.012–0.016 inches (0.0305 centimeters), a width of about 0.105 inches (0.267 centimeters), and a width of the legs 33 and 34 of about 0.035 inches (0.089 centimeters). The hole 36 may have a diameter of 0.035 inches (0.089 centimeters).

Figure 5:
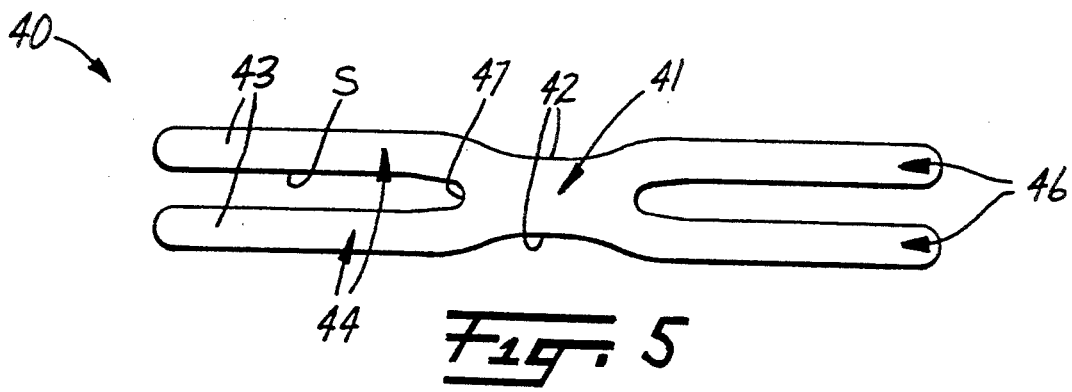
FIG. 5 is a plan view of a blank that may be used to form a third embodiment of surgical clip according to the present invention, illustrating clip applier bearing surfaces.

Referring now to FIGS. 5 and 13 of the drawing, there is shown a third alternative embodiment of a surgical clip according to the present invention, generally designated by the reference numeral 40 which has many parts that are essentially the same as the parts of the clip 30.

Like the clip 30, the clip 40 comprises a unitary, monolithic hinge portion 41 having removal surfaces 42 adapted to be engaged by the tool 4 for removing the clip 40 from the tubular structure. The clip 40 has a first leg portion having a pair of first legs 44 projecting from the hinge portion 41. The first legs 44 have proximal and distal ends, vessel engaging surfaces 45, and clip applier bearing surfaces 43 opposite the vessel engaging surfaces 45.

The first legs 44 are generally parallel and are spaced apart a first distance to provide a vessel tissue extrusion slot S extending between and opening through the vessel engaging 45 and clip applier bearing surfaces 43. The slot S has first 47 and second ends. The first end 47 is a closed end formed by the hinge portion 41. The second end of the slot S of the clip 40 is an open end.

The clip 40 also has a second leg portion having two second legs 46 projecting from the hinge portion 41 and away from the first leg portion. The second legs 46 are generally identical to the first legs 44 so that the clip 40 is symmetrical about an imaginary line through the center of the hinge portion 41. The second legs 46 have proximal and distal ends, vessel engaging surfaces 45A, and clip applier bearing surfaces opposite the vessel engaging surfaces 45A. Like the clip 30, the clip 40 is generally plastically deformable between an unclamped position and a clamped position.

Unlike the hinge portion 31 of the clip 30, the hinge portion 41 of the clip 40 has no circular hole extending therethrough. Also unlike the clip 30, in the clip 40, the first legs 44 have surfaces defining an outer leg width, the hinge portion has outer surfaces defining a hinge portion width H (FIG. 4), and the outer leg width W is generally greater than the hinge portion width H.

As an example not intended to be limiting, the clip 40 may have an overall length of approximately 0.696 inches (1,768 centimeters), a length of the hinge portion 41 of about 0.048 inches (0.122 centimeters), an overall thickness of about 0.012–0.016 inches (0.0305 centimeters), a width of about 0.105 inches (0.267 centimeters), and a width of the legs 44 and 46 of about 0.035 inches (0.064 centimeters). Another version of this example may have a longer hinge portion 41, and correspondingly, a shorter slot S.

Figure 6:
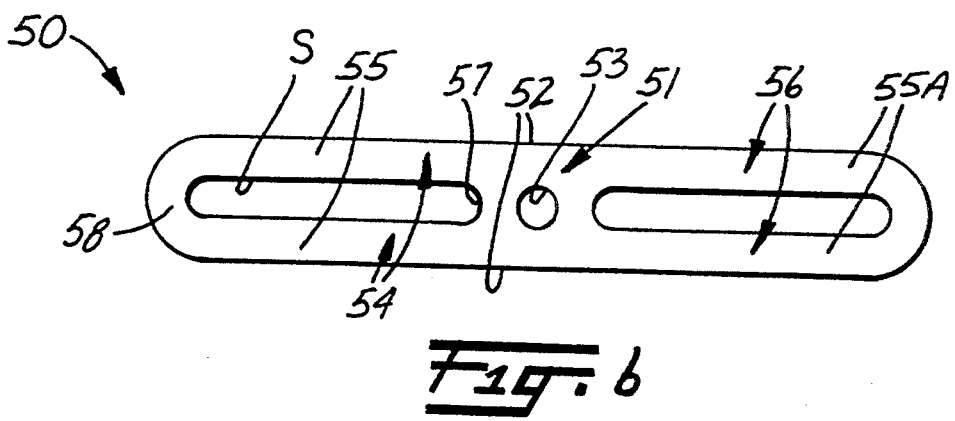
FIG. 6 is a plan view of a blank that may be used to form a fourth embodiment of surgical clip according to the present invention, illustrating vessel engaging surfaces.

Referring now to FIG. 6 of the drawing, there is shown a fourth alternative embodiment of a surgical clip according to the present invention, generally designated by the reference numeral 50 which has many parts that are essentially the same as the parts of the clip 30.

Like the clip 30, the clip 50 comprises a unitary, monolithic hinge portion 51 having removal surfaces 52 adapted to be engaged by the tool 4 for removing the clip 50 from the tubular structure. The clip 50 has a first leg portion having a pair of first legs 54 projecting from the hinge portion 51.

The first legs 54 have proximal and distal ends, vessel engaging surfaces 55, and clip applier bearing surfaces opposite the vessel engaging surfaces 55. The first legs 54 are spaced apart a first distance to provide a vessel tissue extrusion slot S extending between and opening through the vessel engaging 55 and clip applier bearing surfaces. The slot S has first 57 and second ends. The first end 57 is a closed end formed by the hinge portion 51.

Unlike the clip 30, in the clip 50, the second end of the slot S is a closed end formed by a distal end portion 58 similar to the distal end portion 19. Also unlike the clip 30, in the clip 50, the hinge portion 51 includes a circular hole 53 similar to the hole 36.

The clip 50 also has a second leg portion having two second legs 56 projecting from the hinge portion 51 and away from the first leg portion. The second legs 56 are generally identical to the first legs 54 so that the clip 50 is symmetrical about an imaginary line through the center of the hinge portion 51. The second legs 56 have proximal and distal ends, vessel engaging surfaces 55A, and clip applier bearing surfaces opposite the vessel engaging surfaces 55A. Like the clip 30 the clip 50 is generally plastically deformable between an unclamped position and a clamped position.

As an example not intended to be limiting, the clip 50 may have an overall length of approximately 0.696 inches (1.768 centimeters), a length of the hinge portion 51 of about 0.056 inches (0.142 centimeters), an overall thickness of about 0.012–0.016 inches, a width of about 0.105 inches (0.267 centimeters), and a width of the legs 54 and 56 of about 0.035 inches (0.089 centimeters).

Figure 7:
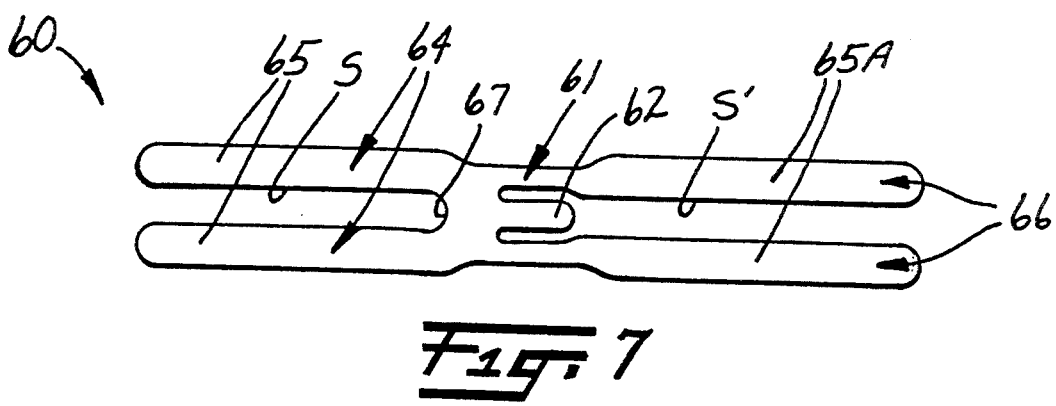
FIG. 7 is a plan view of a blank that may be used to form a fifth embodiment of surgical clip according to the present invention, illustrating vessel engaging surfaces.

Referring now to FIG. 7 of the drawing, there is shown a fifth alternative embodiment of a surgical clip according to the present invention, generally designated by the reference numeral 60 which has many parts that are essentially the same as the parts of the clip 40.

The clip 60 has a hinge portion 61 different than the hinge portion of the clip 40. The unitary, monolithic hinge portion 61 has a removal tab portion 62 having surfaces adapted to be engaged by the tool 4 for removing the clip 40.

The removal tab portion 62 is situated generally at a middle portion of the hinge portion 61 and the clip 60 so that the clip removal tool 4 may provide a generally symmetrical force to remove the clip 60 from the vessel without undue twisting or rotation. Additionally, the removal tab 62 provides a thin portion that may be conveniently grasped by the clip removal tool 4 without undue opening of the jaws of the clip removal tool 4. Limiting the opening of the jaws of the clip removal tool affords easier, more convenient removal of the clip 60 from the body cavity. This is particularly important when the removal must be made through a cannula or access tube (such as the access tube or cannula described in U.S. patent application Ser. No. 07/657,105, now U.S. Pat. No. 5,152,754 or U.S. Pat. No. 5,066,288) used during laparoscopic surgery.

Like the clip 40, the clip 60 comprises a first leg portion having a pair of first legs 64 projecting from the hinge portion 61. The first legs 64 have proximal and distal ends, vessel engaging surfaces 65, and clip applier bearing surfaces opposite the vessel engaging surfaces 65. The first legs 64 are spaced apart a first distance to provide a vessel tissue extrusion slot S extending between and opening through the vessel engaging 65 and clip applier bearing surfaces. The slot S has first 67 and second ends. The first end 67 is a closed end formed by the hinge portion 61. The second end of the slot S of the clip 60 is an open end.

The clip 60 also has a second leg portion having two second legs 66 projecting from the hinge portion 61 and away from the first leg portion. The second legs 66 have proximal and distal ends, vessel engaging surfaces 65A, and clip applier bearing surfaces opposite the vessel engaging surfaces 65A. Like the clip 40, the clip 60 is generally plastically deformable between an unclamped position and a clamped position.

The slot S' situated between the second legs 66 extends farther into the hinge portion 61 than the slot S between the first legs 64. Such a geometry affords greater access to the removal tab portion 62 for the clip removal tool 4.

The removal tab portion 62 is adapted to project in generally the same direction that the first and second legs project when the clip is in the clamped position. The removal tab portion 62 affords a convenient structure to grasp with the clip removal tool 4.

As an example not intended to be limiting, the clip 60 may have an overall length of approximately 0.696 inches (1.768 centimeters), a length of the hinge portion 61 of about 0.103 inches, (0.2616 centimeters), an overall thickness of about 0.012–0.016 inches (0.0305–0.0406 centimeters), a width of about 0.105 inches (0.267 centimeters), and a width of the legs 64 and 66 of about 0.035 inches (0.089 centimeters). The tab portion 62 has a width of approximately 0.025 inches (0.064 centimeters) and a length of about 0.052 inches (0.132 centimeters).

Figure 8:
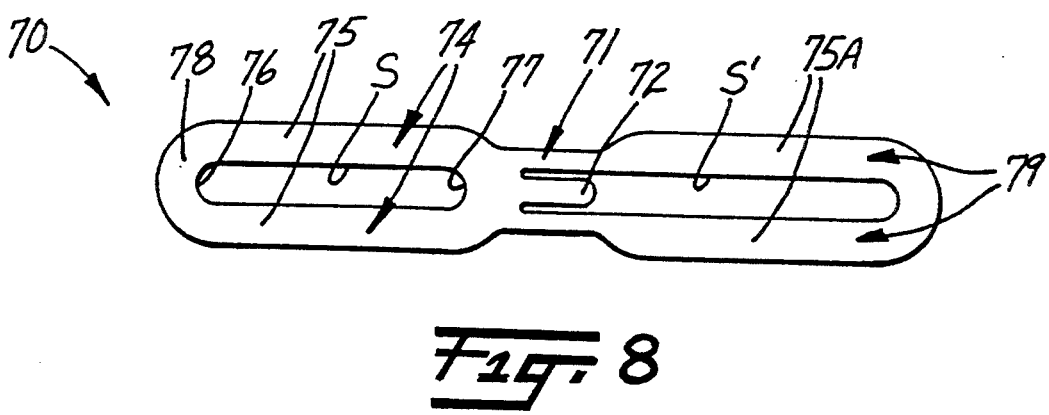
FIG. 8 is a plan view of a blank that may be used to form a sixth embodiment of surgical clip according to the present invention, illustrating vessel engaging surfaces.

Referring now to FIG. 8 of the drawing, there is shown a sixth alternative embodiment of a surgical clip according to the present invention, which is similar to the clip 60 and generally designated by the reference numeral 70.

The clip 70 has a unitary, monolithic hinge portion 71 having a removal tab portion 72 having surfaces adapted to be engaged by the tool 4 for removing the clip 70.

Like the clip 60, the clip 70 comprises a first leg portion having a pair of first legs 74 projecting from the hinge portion 71. The first legs 74 have proximal and distal ends, vessel engaging surfaces 75, and clip applier bearing surfaces opposite the vessel engaging surfaces 75. The first legs 74 are spaced apart a first distance to provide a vessel tissue extrusion slot S extending between and opening through the vessel engaging 75 and clip applier bearing surfaces.

The slot S has first 77 and second 76 ends. The first end 77 is a closed end formed by the hinge portion 71. The second end of the slot S of the clip 70 is also a closed end and is formed by the arcuate distal end portion 78.

The clip 70 also has a second leg portion having two second legs 79 projecting from the hinge portion 71 and away from the first leg portion. The second legs 79 have proximal and distal ends, vessel engaging surfaces 75A, and clip applier bearing surfaces opposite the vessel engaging surfaces 75A. Like the clip 60 the clip 70 is generally plastically deformable between an unclamped position and a clamped position.

The slot S' situated between the second legs 79 extends farther into the hinge portion 71 than the slot S between the first legs 74. Such a geometry affords greater access to the removal tab portion 72 for the clip removal tool 4 and affords a view of the vessel 8 through the hinge portion 71.

As an example not intended to be limiting, the clip 70 may have an overall length of approximately 0.696 inches (1.768 centimeters), a length of the hinge portion 71 of about 0.088 inches, (0.224 centimeters), an overall thickness of about 0.012–0.016 inches, a width of about 0.105 inches (0.267 centimeters), and a width of the legs 74 and 79 of about 0.035 inches (0.064 centimeters). The tab portion 72 has a length of about 0.055 inches (0.140 centimeters).

Figure 9:
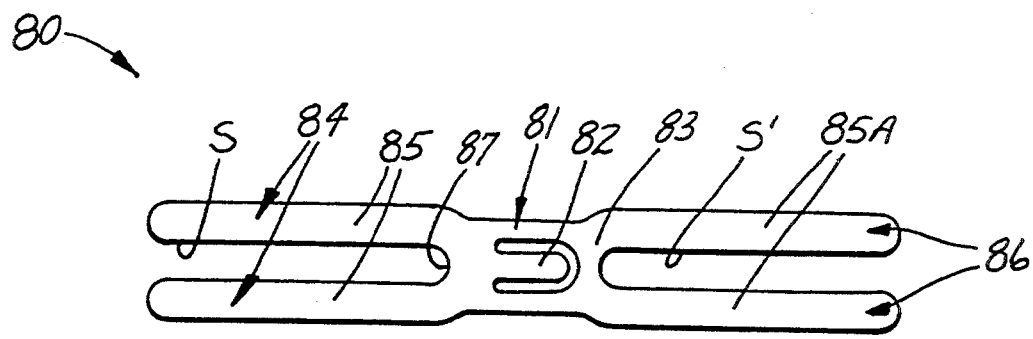
FIG. 9 is a plan view of a blank that may be used to form a seventh embodiment of surgical clip according to the present invention, illustrating vessel engaging surfaces.

Referring now to FIG. 9 of the drawing, there is shown a seventh alternative embodiment of a surgical clip according to the present invention, similar to the clip 60 and generally designated by the reference numeral 80.

The clip 80 has a hinge portion 81 slightly different than the hinge portion of the clip 60 which will be explained more fully below. The unitary, monolithic hinge portion 81 has a removal tab portion 82 having surfaces adapted to be engaged by the tool 4 for removing the clip 80.

Like the clip 60, the clip 80 comprises a first leg portion having a pair of first legs 84 projecting from the hinge portion 81. The first legs 84 have proximal and distal ends, vessel engaging surfaces 85, and clip applier bearing surfaces opposite the vessel engaging surfaces 85. The first legs 84 are spaced apart a first distance to provide a vessel tissue extrusion slot S extending between and opening through the vessel engaging 85 and clip applier bearing surfaces. The slot S has first 87 and second ends. The first end 87 is a closed end formed by the hinge portion 81. The second end of the slot S of the clip 80 is an open end.

The clip 80 also has a second leg portion having two second legs 86 projecting from the hinge portion 81 and away from the first leg portion. The second legs 86 have proximal and distal ends, vessel engaging surfaces 85A, and clip applier bearing surfaces opposite the vessel engaging surfaces 85A. Like the clip 60 the clip 80 is generally plastically deformable between an unclamped position and a clamped position.

Unlike the clip 60, in the clip 80, the slot S' situated between the second legs 86 extends into the hinge portion 81 approximately the same amount as the slot S between the first legs 84 extends into the hinge portion 81. The end of the slot S' is formed by hinge end portion 83. A hinge portion 81 which incorporates a hinge end portion 83 resists bending and twisting of the clip 80 when the clip removal tool 4 grasps the clip 80 to remove it from a vessel 8. Such a hinge portion 81 also resists collapse when the clip removal tool 4 grasps the clip 80.

Figure 10:
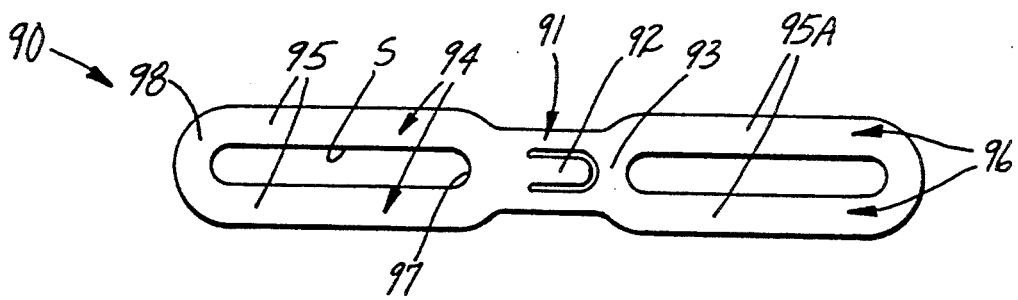
FIG. 10 is a plan view of a blank that may be used to form an eighth embodiment of surgical clip according to the present invention, illustrating vessel engaging surfaces.

Referring now to FIG. 10 of the drawing, there is shown a eighth alternative embodiment of a surgical clip according to the present invention, similar to the clip 80 and generally designated by the reference numeral 90.

Like the clip 80, the clip 90 has a unitary monolithic hinge portion 91 having an end portion 93 and a tab portion 92. The clip 90 comprises a first leg portion having a pair of first legs 94 projecting from the hinge portion 91. The first legs 94 have proximal and distal ends, vessel engaging surfaces 95, and clip applier bearing surfaces opposite the vessel engaging surfaces 95.

The first legs 94 are generally parallel and spaced apart a first distance to provide a vessel tissue extrusion slot S extending between and opening through the vessel engaging 95 and clip applier bearing surfaces. The slot S has first 97 and second ends. The first end 97 is a closed end formed by the hinge portion 91. The second end of the slot S of the clip 90 is also a closed end formed by arcuate distal end portion 98.

The clip 90 also has a second leg portion having two second legs 96 projecting from the hinge portion 91 and away from the first leg portion. The second legs 96 have proximal and distal ends, vessel engaging surfaces 95A, and clip applier bearing surfaces opposite the vessel engaging surfaces 95A. Like the clip 80 the clip 90 is generally plastically deformable between an unclamped position and a clamped position.

Figure 11:
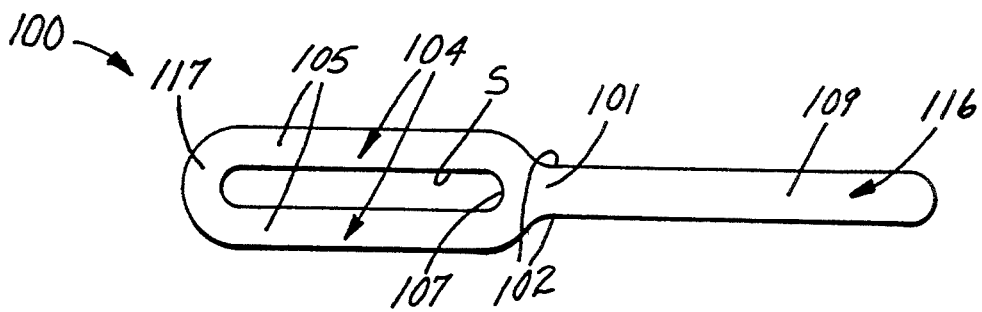
FIG. 11 is a plan view of a blank that may be used to form a ninth embodiment of surgical clip according to the present invention, illustrating vessel engaging surfaces.

Referring now to FIGS. 11 and 14 of the drawing, there is shown a ninth alternative embodiment of a surgical clip according to the present invention, generally designated by the reference numeral 100.

The clip 100 has a unitary monolithic hinge portion 101 having clip removal tool engaging surfaces 102. The clip 100 comprises a first leg portion having a pair of first legs 104 projecting from the hinge portion 101. The first legs 104 have proximal and distal ends, vessel engaging surfaces 105, and clip applier bearing surfaces 106 opposite the vessel engaging surfaces 105.

The first legs 104 are generally parallel and spaced apart a first distance to provide a vessel tissue extrusion slot S extending between and opening through the vessel engaging 105 and clip applier bearing surfaces 106. The slot S has first 107 and second ends. The first end 107 is a closed end formed by the hinge portion 101. The second end of the slot S of the clip 100 is also a closed end formed by arcuate distal end portion 117.

Unlike any of the previously described clips, the clip 100 also has a second leg portion having only one second leg 116 projecting from the hinge portion 101 and away from the first leg portion. The second leg 116 has proximal and distal ends, vessel engaging surface 109, and clip applier bearing surface 110 opposite the vessel engaging surface 109. The clip 100 is generally plastically deformable between an unclamped position and a clamped position.

The vessel engaging surface 109 is adapted to engage the tissue of the vessel 8 and to cause portions of the vessel 8 to extrude into the slot S and to form a tortuous shape.

Referring now to FIG. 17 of the drawing, there is shown a tenth alternative embodiment of a surgical clip according to the present invention, generally designated by the reference numeral 10′ which has many parts that are essentially the same as the parts of the clip 10 to which a prime "′" has been added.

Like the clip 10, the clip 10′ comprises a unitary, monolithic hinge portion 11′ having removal surfaces 12′ adapted to be engaged by the tool 4 for removing the clip 10′ from the tubular structure. The clip 10′ has a first leg portion having a pair of first legs 14′ projecting from the hinge portion 11′. The first legs 14′ have proximal and distal ends, vessel engaging surfaces 16′, and clip applier bearing surfaces opposite the vessel engaging surfaces 16′. The first legs 14′ are spaced apart a first distance to provide a vessel tissue extrusion slot S extending between and opening through the vessel engaging 16′ and clip applier bearing surfaces. The slot S has first 17′ and second 18′ closed ends.

The first legs 14′ are generally parallel to each other. The distal ends of the first legs 14′ are connected by an arcuate distal end portion 19′ and are integral therewith. The arcuate distal end portion 19′ forms the second, closed end 18′ of the slot S.

The clip 10′ also has a second leg portion having two second legs 20′ projecting from the hinge portion 11′ and away from the first leg portion. The second legs 20′ have proximal and distal ends, vessel engaging surfaces, and clip applier bearing surfaces opposite the vessel engaging surfaces. Like the clip 10 the clip 10′ is generally plastically deformable between an unclamped position and a clamped position.

Unlike the clip 10, in the clip 10′ the second end of the slot between the second legs 20′ is an open end. Also unlike the clip 10, the clip 10′ is not symmetrical about an axis which is perpendicular to the longitudinal axis of the clip 10′ and which passes through a middle portion of the clip.

The absence of a distal end portion for the legs 20′ in the clip 10 is believed to provide a clip that is more readily removable from a tubular structure than the clip 10. Additionally, the presence of the distal end portion 19′ affords a convenient structure that may be used by the internal structure of a clip applier to advance or feed the clip 10′ to the clip closing jaws. The clip 10′ is believed to combine many of the desirable features of both the clip 10 and the clip 30.

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A surgical clip for occluding a tubular tissue structure, said clip comprising:

a monolithic hinge portion having surfaces adapted to be engaged by a clip removal tool for removing the clip from the tubular tissue structure, a first leg portion having a pair of first legs projecting from the hinge portion, said first legs having proximal and distal ends, tissue engaging surfaces, and clip applier bearing surfaces opposite said tissue engaging surfaces, said pair of first legs being spaced apart a first distance to provide a tissue extrusion slot extending between and opening through said tissue engaging and clip applier bearing surfaces, said tissue extrusion slot having a first end with said first end being a closed end formed by said hinge portion, a second leg portion having at least one second leg projecting from said hinge portion, said at least one second leg having proximal and distal ends, a tissue engaging surface, and a clip applier bearing surface opposite said tissue engaging surface, said clip being generally plastically deformable between an unclamped position with said tissue engaging surface of said second leg portion being spaced from said tissue engaging surfaces of said first leg portion and a clamped position with said tissue engaging surfaces of said first and second leg portions being spaced closer together than in said unclamped position, with the tubular tissue structure compressed between said tissue engaging surfaces of said first and second leg portions, and with tissue situated within said tissue extrusion slot, said hinge portion having structure located between said first legs to define said closed first end of said tissue extrusion slot, and said surfaces adapted to be engaged by a clip removal tool being situated so that the clip removal tool may provide a removal force to afford removal of said clip from said tubular tissue structure when said clip is in said clamped position, and wherein said tissue extrusion slot has a second end, and said second end of said slot is an open end.

2. A surgical clip according to claim 1 wherein said clip applier bearing surfaces and said tissue engaging surfaces of said first and second leg portions are generally planar portions.

3. A surgical clip according to claim 1 wherein said second leg portion has two second legs projecting from said hinge portion.

4. A surgical clip according to claim 1 wherein said second leg portion has one second leg projecting from said hinge portion.

5. A surgical clip according to claim 1 wherein said first legs have surfaces defining an outer leg width, and said hinge portion has outer surfaces defining a hinge portion width, and said outer leg width is substantially equal to said hinge portion width.

6. A surgical clip according to claim 1 wherein said hinge portion comprises a (removal) tab portion having surfaces adapted to be engaged by the tool for removing the clip.

7. A surgical clip according to claim 6 wherein said removal tab portion is adapted to project away from the first and second legs when the clip is in the clamped position.

8. A surgical clip for occluding a tubular tissue structure, said clip comprising:

a monolithic hinge portion having surfaces adapted to be engaged by a clip removal tool for removing the clip from the tubular tissue structure, a first leg portion having a pair of first legs projecting from the hinge portion, said first legs having proximal and distal ends, tissue engaging surfaces, and clip applier bearing surfaces opposite said tissue engaging surfaces, said pair of first legs being spaced apart a first distance to provide a tissue extrusion slot extending between and opening through said tissue engaging and clip applier bearing surfaces, said tissue extrusion slot having a first end with said first end being a closed end formed by said hinge portion, a second leg portion having at least one second leg projecting from said hinge portion, said at least one second leg having proximal and distal ends, a tissue engaging surface, and a clip applier bearing surface opposite said tissue engaging surface, said clip being generally plastically deformable between an unclamped position with said tissue engaging surface of said second leg portion being spaced from said tissue engaging surfaces of said first leg portion and a clamped position with said tissue engaging surfaces of said first and second leg portions being spaced closer together than in said unclamped position, with the tubular tissue structure compressed between said tissue engaging surfaces of said first and second leg portions, and with tissue situated within said tissue extrusion slot, said hinge portion having structure located between said first legs to define said closed first end of said tissue extrusion slot, and said surfaces adapted to be engaged by a clip removal tool being situated so that the clip removal tool may provide a removal force to afford removal of said clip from said tubular tissue structure when said clip is in said clamped position, and wherein said hinge portion includes a circular hole extending therethrough.

9. A surgical clip for occluding a tubular tissue structure, said clip comprising:

a monolithic hinge portion having surfaces adapted to be engaged by a clip removal tool for removing the clip from the tubular tissue structure, a first leg portion having a pair of first legs projecting from the hinge portion, said first legs having proximal and distal ends, tissue engaging surfaces, and clip applier bearing surfaces opposite said tissue engaging surfaces, said pair of first legs being spaced apart a first distance to provide a tissue extrusion slot extending between and opening through said tissue engaging and clip applier bearing surfaces, said tissue extrusion slot having a first end with said first end being a closed end formed by said hinge portion, a second leg portion having at least one second leg projecting from said hinge portion, said at least one second leg having proximal and distal ends, a tissue engaging surface, and a clip applier bearing surface opposite said tissue engaging surface, said clip being generally plastically deformable between an unclamped position with said tissue engaging surface of said second leg portion being spaced from said tissue engaging surfaces of said first leg portion and a clamped position with said tissue engaging surfaces of said first and second leg portions being spaced closer together than in said unclamped position, with the tubular tissue structure compressed between said tissue engaging surfaces of said first and second leg portions, and with tissue situated within said tissue extrusion slot, said hinge portion having structure located between said first legs to define said closed first end of said tissue extrusion slot, and said surfaces adapted to be engaged by a clip removal tool being situated so that the clip removal tool may provide a removal force to afford removal of said clip from said tubular tissue structure when said clip is in said clamped position, and wherein said first legs have surfaces defining an outer leg width, and said hinge portion has outer surfaces defining a hinge portion width, and said outer leg width is substantially greater than said hinge portion width.

10. A surgical clip according to claim 9 wherein said distal ends of said first legs of said first leg portion are connected by a distal end portion, said tissue extrusion slot has a second end, and said second end of said tissue extrusion slot is a closed end formed by said distal end portion.

11. A surgical clip according to claim 10 wherein said distal end portion is an arcuate portion, and said first legs are generally parallel to one another.

12. A surgical clip for occluding a tubular tissue structure, said clip comprising:

a hinge portion having surfaces adapted to be engaged by a tool for removing the clip from the tubular tissue structure, a first leg portion having a pair of first legs projecting from the hinge portion, said first legs having proximal and distal ends, tissue engaging surfaces, and clip applier bearing surfaces opposite said tissue engaging surfaces, said pair of first legs being spaced apart a first distance to provide a tissue extrusion slot extending between and opening through said tissue engaging and clip applier bearing surfaces, said tissue extrusion slot having a first end with said first end being a closed end, a second leg portion having at least one second leg projecting from said hinge portion, said at least one second leg having proximal and distal ends, a tissue engaging surface, and a clip applier bearing surface opposite said tissue engaging surface, said clip being generally plastically deformable between an unclamped position with said tissue engaging surface of said second leg portion being spaced from said tissue engaging surfaces of said first leg portion and a clamped position with said tissue engaging surfaces of said first and second leg portions being spaced closer together than in said unclamped position, with the tubular tissue structure compressed between said tissue engaging surfaces of said first and second leg portions, and with tissue situated within said tissue extrusion slot, wherein when the clip is in the clamped position, the clip may be removed from the tubular tissue structure by having the tool for removing the clip grasp the clip and pull the clip from the tubular tissue structure, and wherein said hinge portion includes a circular hole extending therethrough.

13. A method of occluding a tubular tissue structure with a surgical clip, said clip comprising a hinge portion; a first leg portion having a pair of first legs projecting from the hinge portion; said first legs having proximal and distal ends, tissue engaging surfaces, and clip applier bearing surfaces opposite said tissue engaging surfaces; said pair of first legs being spaced apart a first distance to provide a tissue extrusion slot extending between and opening through said tissue engaging and clip applier bearing surfaces, said tissue extrusion slot having a first end with said first end being a closed end;

a second leg portion having at least one second leg projecting from said hinge portion, said at least one second leg having proximal and distal ends, a tissue engaging surface, and a clip applier bearing surface opposite said tissue engaging surface; said clip also having adapted to be engaged by a surgical tool for removing the clip from the tubular tissue structure;

said method including the steps of:

(1) compressing the tubular tissue structure between said tissue engaging surfaces of said first and second leg portions by plastically deforming the surgical clip onto the tubular tissue structure by moving the clip from (a) an unclamped position with said tissue engaging surface of said second leg portion being spaced from said tissue engaging surfaces of said first leg portion, to (b) a clamped position with said tissue engaging surfaces of said first and second leg portions being spaced closer together than in said unclamped position, and with tissue situated within said tissue extrusion slot, and (2) then removing the clip from the tubular tissue structure when the clip is in the clamped position by grasping the clip with a surgical tool and pulling the clip from the tubular tissue structure.

14. A method according to claim 13 wherein the step of removing the clip from the tubular tissue structure when the clip is in the clamped position comprises the step of:

grasping the clip on the hinge portion of the clip with a tool for removing the clip, 15. A method according to claim 13 wherein the step of removing the clip from the tubular tissue structure when the clip is in the clamped position comprises the step of:

removing the clamped clip from the tubular tissue structure with the surgical tool without the surgical tool engaging the distal ends of the first and second leg portions.

16. A method according to claim 13 wherein the step of compressing the tubular tissue structure between said tissue engaging surfaces includes the step of threading the surgical clip through a cannula during a laparoscopic surgical procedure.

* * * * *